US012653826B2

(12) United States Patent
Brent et al.

(10) Patent No.: US 12,653,826 B2
(45) Date of Patent: Jun. 16, 2026

(54) METHODS OF REDUCING THE LIKELIHOOD OF CARCINOID HEART DISEASE IN PATIENTS WITH NEUROENDOCRINE TUMORS

(71) Applicant: TerSera Therapeutics LLC, Deerfield, IL (US)

(72) Inventors: Lonnie Brent, Deerfield, IL (US); Janine North, Eugene, OR (US)

(73) Assignee: TerSera Therapeutics LLC, Deerfield, IL (US)

( * ) Notice: Subject to any disclaimer, the term of this patent is extended or adjusted under 35 U.S.C. 154(b) by 0 days.

(21) Appl. No.: 18/183,247

(22) Filed: Mar. 14, 2023

(65) Prior Publication Data

US 2023/0310434 A1 Oct. 5, 2023

Related U.S. Application Data

(60) Provisional application No. 63/326,463, filed on Apr. 1, 2022.

(51) Int. Cl.

| | |
|---|---|
| ***A61K 31/506*** | (2006.01) |
| ***A61B 5/00*** | (2006.01) |
| ***A61K 38/31*** | (2006.01) |
| ***A61P 35/00*** | (2006.01) |

(52) U.S. Cl.

CPC .......... *A61K 31/506* (2013.01); *A61B 5/4848* (2013.01); *A61K 38/31* (2013.01); *A61P 35/00* (2018.01)

(58) Field of Classification Search

CPC .... A61K 31/506; A61K 38/31; A61B 5/4848; A61P 35/00

See application file for complete search history.

(56) References Cited

U.S. PATENT DOCUMENTS

| | | | | |
|---|---|---|---|---|
| 7,553,840 | B2 | 6/2009 | Devasagayaraj et al. | |
| 7,709,493 | B2 | 5/2010 | Devasagayaraj et al. | |
| 8,193,204 | B2 | 6/2012 | Bednarz et al. | |
| 8,653,094 | B2 | 2/2014 | Bednarz et al. | |
| 2021/0353624 | A1* | 11/2021 | Gopinathan ....... | A61K 31/7068 |

OTHER PUBLICATIONS

Agha, Ali M., et al. "Multimodality Imaging in Carcinoid Heart Disease." Open Heart, vol. 6, No. 1, Jun. 2019, p. e001060. openheart.bmj.com, https://doi.org/10.1136/openhrt-2019-001060. (Year: 2019).*

Zacks, et al. "Telotristat etiprate appears to halt carcinoid heart disease." ENETS 2016 Poster [https://carcinoidheart.com/wp-content/uploads/2016/06/ENETS-2016-Poster-Final.pdf] (Year: 2016).*

Maroun, J., et al. "Guidelines for the Diagnosis and Management of Carcinoid Tumours. Part 1: The Gastrointestinal Tract. A Statement from a Canadian National Carcinoid Expert Group." Current Oncology, vol. 13, No. 2, Apr. 2006, pp. 67-76. (Year: 2006).*

Møller, Jacob E., et al. "Prognosis of Carcinoid Heart Disease: Analysis of 200 Cases Over Two Decades." Circulation, vol. 112, No. 21, Nov. 2005, pp. 3320-3327. DOI.org (Crossref), https://doi.org/10.1161/CIRCULATIONAHA.105.553750. (Year: 2005).*

Hota et al, First UK Real-Word [World] Data on Patients with Carcinoid Syndrome on Long-Term Telotristat Therapy, Gut 2021;70(Suppl 1):A1-A262, p. A173. (Year: 2021).*

Kulke, M., et al.; "Telotristat Ethyl, a Tryptophan Hydroxylase Inhibitor for the Treatment of Carcinoid Syndrome"; Journal of Clinical Oncology, vol. 35, Issue No. 1; 2016; pp. 14-23.

Pavel, M., et al.; "Telotristat ethyl in carcinoid syndrome: safety and efficacy in the Telecast phase 3 trial"; Endocrine-Related Cancer, vol. 25, Issue No. 3; 2018; pp. 309-322.

Dias, Andre Roncon, et al. Gastric Neuroendocrine Tumor: Review and Update, ABCD Arq Bras Cir Dig, 2017; 30(2): 150-154.

Definition of Newly. Webster's Unabridged Dictionary of the English Language. RHR Press. ISBN 0-681-31723-X.

Ito, Tetsuhide, et al. JNETS clinical practice guidelines for gastroenteropancreatic neuroendocrine neoplasms: diagnosis, treatment, and follow-up: a synopsis, J Gastroenterol, 2021, 56: 1033-1044.

Milanetto, Anna Caterina et al. Serotonin-Secreting Neuroendocrine Tumours of the Pancreas, J. Clin. Med. 2020, 9, 1363: 1-9.

Pavel, Marianne, et al. Telotristat ethyl in carcinoid syndrome: safety and efficacy in the Telecast phase 3 trial, Endocrine-Related Cancer, 2020, 25, 309-322.

Cancer: Active v. Historical. A Premera Blue Cross Blue Shield of Alaska Documentation and Coding Series for Providers. Dec. 15, 2022. https://www.premera.com/documents/047551.pdf.

Maryland Oncology Hematology. Treatments & Services, Newly Diagnosed. Website. *Newly Diagnosed—Maryland Oncology Hematology*, printed Jul. 8, 2025.

Das et al., Carcinoid Heart Disease Management: A Multi-Disciplinary Collaboration, *The Oncologist*, 2023, pp. 1-9, https://doi.org/10.1093/oncolo/oyad126.

International Search Report and Written Opinion dated Jun. 1, 2023, for PCT Application No. PCT/US2023/014564, pp. 1-14.

Hota et all, First UK Real-Word [World] Data on Patients with Carcinoid Syndrome on Long-Term Telotristat Therapy, Gut 2021;70(Suppl 1):A1-A262, p. A173.

(Continued)

*Primary Examiner* — Clinton A Brooks

*Assistant Examiner* — Kyle Nottingham

(74) *Attorney, Agent, or Firm* — Karen LeCuyer; DeWitt LLP

(57) ABSTRACT

Described herein are methods of treating a human patient with a newly diagnosed neuroendocrine tumor, methods of treating patients with neuroendocrine tumors with early signs of carcinoid heart disease who have not had a heart valve replacement, and methods of treating a human patient with the neuroendocrine tumor who has had a recent heart valve replacement. Administering telotristat ethyl to these patients can reduce the development of carcinoid heart disease and improve clinical outcomes.

8 Claims, No Drawings

(56) References Cited

OTHER PUBLICATIONS

Oleinikov K, Korach A, Planer D, Gilon D, Grozinsky-Glasberg S. Update in carcinoid heart disease—the heart of the matter. Rev Endocr Metab Disord. Sep. 2021;22(3):553-561. doi: 10.1007/s11154-020-09624-y. Epub Jan. 14, 2021. PMID: 33443717.

Oleinikov K, Avniel-Polak S, Gross DJ, Grozinsky-Glasberg S. Carcinoid Syndrome: Updates and Review of Current Therapy. Curr Treat Options Oncol. Jul. 9, 2019;20(9):70. doi: 10.1007/s11864-019-0671-0. PMID: 31286272.

Hassan SA, Palaskas NL, Agha AM, Iliescu C, Lopez-Mattei J, Chen C, Zheng H, Yusuf SW. Carcinoid Heart Disease: a Comprehensive Review. Curr Cardiol Rep. Nov. 19, 2019;21(11):140. doi: 10.1007/s11886-019-1207-8. PMID: 31745664.

* cited by examiner

METHODS OF REDUCING THE LIKELIHOOD OF CARCINOID HEART DISEASE IN PATIENTS WITH NEUROENDOCRINE TUMORS

CROSS-REFERENCE TO RELATED APPLICATIONS

This application claims priority to U.S. Provisional Application 63/326,463 filed on Apr. 1, 2022, which is incorporated herein by reference in its entirety.

FIELD OF THE DISCLOSURE

The present disclosure is related to methods of treating patients with neuroendocrine tumors and reducing the likelihood of these patients developing carcinoid heart disease (CaHD).

BACKGROUND

Telotristat ethyl ((S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate; TE) is commercially available as XERMELO®, which is US FDA approved for the treatment of carcinoid syndrome diarrhea in combination with somatostatin analog (SSA) therapy in adults inadequately controlled by SSA therapy. TE is a tryptophan hydroxylase inhibitor and telotristat, the active metabolite, mediates the rate-limiting step in serotonin biosynthesis. By inhibiting tryptophan hydroxylase, TE and its metabolite reduce the production of peripheral serotonin and also the frequency of carcinoid syndrome diarrhea.

As described in Kulke et al. ("Telotristat Ethyl, a Tryptophan Hydroxylase Inhibitor for the Treatment of Carcinoid Syndrome", Journal of Clinical Oncology, 35(1), pp. 14-23, 2016) describes the phase III TELESTAR study assessing the safety and efficacy of TE dosed at 250 or 500 mg three times daily in patients with carcinoid syndrome not adequately controlled with SSA therapy. The patients in the TELESTAR study had well differentiated metastatic neuroendocrine tumors, a documented history of CS, were on stable dose SSA for at least 3 months prior to enrollment. TE both reduced urinary 5-HIAA levels and frequency of bowel movements.

As described in Pavel et al. (Endocrine-Related Cancer, Vol. 25, pp. 309-322, (2018)), in the phase 3 TELECAST study, TE dosed at 250 or 500 mg three times daily was effective when added to SSAs to treat patients with carcinoid syndrome (CS) diarrhea. Of particular note, the patients in the TELECAST study had well differentiated metastatic neuroendocrine tumors, a documented history of CS, were on stable dose SSA for at least 3 months prior to enrollment, and had one or more specified symptoms of CS. TE both reduced urinary 5-HIAA levels and frequency of bowel movements, thus TE was US FDA approved in combination with SSAs in patients with CS diarrhea.

What is needed are improved methods of treating patients with neuroendocrine tumors.

BRIEF SUMMARY

In an aspect, a method of treating or managing a human patient with a newly diagnosed neuroendocrine tumor comprises periodically, after newly diagnosing the neuroendocrine tumor, measuring a level of 5-hydroxyindoleacetic acid (5-HIAA) in a plasma or urine sample from the patient, and daily administering a therapeutically effective amount of telotristat ethyl when an initial level of 5-HIAA is at least two times greater than or equal to the upper limit of normal (ULN), wherein the ULN is about 22 ng/ml for the plasma sample or 8 mg/24 hours for the urine sample.

In another aspect, a method of treating or managing a human patient with a neuroendocrine tumor comprises determining that the patient has early signs of carcinoid heart disease, measuring a level of 5-hydroxyindoleacetic acid (5-HIAA) in a plasma or urine sample from the patient, and administering a therapeutically effective amount of telotristat ethyl when the level of 5-HIAA is greater than or equal to the upper limit of normal (ULN), wherein the ULN is about 22 ng/ml for the plasma sample or 8 mg/24 hours for the urine sample, wherein the patient has not had a heart valve replacement, and wherein the patient has not been receiving telotristat ethyl for the treatment of carcinoid syndrome diarrhea.

In yet another aspect, a method of treating or managing a human patient with a neuroendocrine tumor comprises identifying a patient who has had a recent heart valve replacement, and prior to the patient developing symptoms of carcinoid syndrome, administering a therapeutically effective amount of telotristat ethyl.

The above-described and other features will be appreciated and understood by those skilled in the art from the following detailed description, drawings, and appended claims.

DETAILED DESCRIPTION

In the phase 3 TELECAST study, the combination of SSA and TE was studied. The patients in the TELECAST study had well differentiated metastatic neuroendocrine tumors and a documented history of CS. As explained in Pavel et al. (Endocrine-Related Cancer, Vol. 25, pp. 309-322, (2018)) on page 310, elevated levels of serotonin can lead to the development of carcinoid heart disease (CaHD). Pavel et al., however, does not propose methods to reduce the development of CS or CaHD in patients with neuroendocrine tumors. The inventors of the present application have unexpectedly recognized that intervention with TE prior to a documented history of CS can help manage 5-HIAA levels and not only delay the onset of CS, but also reduce the likelihood of these patients developing CaHD. In addition, administration of TE during the early stages of CaHD, but before valve replacement, or after valve replacement, can reduce the risk of further cardiac damage in the patient.

In addition to TE, the compounds described in U.S. Pat. Nos. 7,553,840 and 7,709,493 can be used in the methods described herein.

As used herein, telotristat can be administered as telotristat etiprate, which undergoes hydrolysis to the active compound telotristat. Telotristat ethyl can be in the form of a salt such as telotristat etiprate. Telotristat etiprate is the hippurate salt of telotristat ethyl [(S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate], which undergoes hydrolysis to the active metabolite, (S)-2-amino-3-(4-(2-amino-6-((R)-1-(4-chloro-2-(3-methyl-1H-pyrazol-1-yl) phenyl)-2,2,2-trifluoroethoxy)pyrimidin-4-yl)phenyl)propanoic acid. The molecular formula of telotristat etiprate is $C_{27}H_{26}ClF_3N_6O_3 \cdot C_9H_9NO_3$ and its molecular weight is 754.2. The molecular weight of the free base (telotristat ethyl) is 575.0.

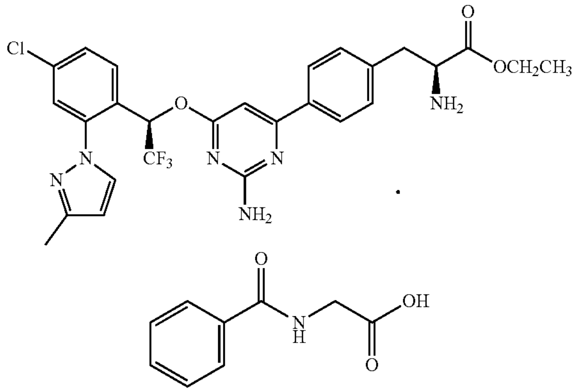

As used herein, salts may be prepared from pharmaceutically acceptable non-toxic acids or bases including inorganic acids and bases and organic acids and bases. Exemplary pharmaceutically acceptable salts include hydroxide, acetate, benzenesulfonate (besylate), benzoate, bicarbonate, bisulfate, carbonate, camphorsulfonate, citrate, ethanesulfonate, fiunarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnarnate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate and the like.

In an aspect, telotristat etipirate is present in a dosage form in solid crystalline form such as that described in U.S. Pat. Nos. 8,193,204 and 8,653,094.

As used herein, neuroendocrine tumors are tumors that originate in the cells of the neuroendocrine system, such as the gastrointestinal tract (large intestine, small intestine, appendix), lung and pancreas. Neuroendocrine tumors include tumors of the lung, liver, pancreas, small bowel, stomach, jejunum, duodenum, ileum, appendix, colon, small bowel mesentery, cecum, rectum, or a combination thereof. The term "carcinoid" has been used to indicate well-differentiated neuroendocrine tumors that secrete serotonin. Carcinoid tumors often spread to other organs including the liver. Overproduction of serotonin by neuroendocrine tumors can be measured by determining the level of the serotonin metabolite, 5-hydroxyindoleacetic acid.

In the early stages of a neuroendocrine tumor, a patient may not have any symptoms. Many neuroendocrine tumors are found when a patient undergoes x-rays or other medical procedures unrelated to the tumor. If a physician suspects a neuroendocrine tumor, a biopsy, endoscopy, imaging such as computed tomography (CT) or magnetic resonance imaging (MRI) scans, or other procedure may be performed to confirm the neuroendocrine tumor.

Upon diagnosis of a neuroendocrine tumor, a patient is typically treated with a somatostatin analog (SSA) such as lanreotide, octreotide, pasireotide, or a combination thereof. The SSAs are believed to have antiproliferative activity, and also help to manage the symptoms of CS as described below.

CS develops in at least about 20% of patients with neuroendocrine tumors. CS is characterized by symptoms including severe diarrhea, flushing, abdominal pain, bronchospasm, cyanosis, hypotension, pellagra, teleangiectasia, and the like.

CaHD is a fibrotic complication of CS which occurs in about 20% or more patients with CS and is typically characterized by abnormalities of the right side of the heart. Substances secreted by the tumor such as serotonin, prostaglandins, histamine, bradykinins and other substances are believed to mediate CaHD, leading to the production of plaque-like deposits primarily on the right side of the heart. The most common complication of CaHD is valvular heart disease, however arrhythmias and metastasis to cardiac tissue amongst other complications may also occur. CaHD may be asymptomatic but may also include symptoms such as fatigue and progressive exertional dyspnoea. Diagnosis is typically made by echocardiogram, and patients with CS are typically periodically checked by echocardiogram for CaHD. Additionally, screening for brain natriuretic peptide (BNP) and N-terminal pro b-type natriuretic peptide (NT-proBNP) can be used to screen CaHD. CaHD is an underlying cause of morbidity and mortality in patients with CS. Currently there are no FDA approved therapies for CaHD and there is a great unmet need for therapies for the treatment and/or reduction of likelihood of CaHD.

As used herein, the terms "subject" and "patient" are used interchangeably. In certain embodiments, the patient is a human.

The terms "treat," "treating" and "treatment" contemplate an action that occurs while a patient is suffering from the specified disease or disorder, which reduces the severity of the disease or disorder or one or more of its symptoms, or retards or slows the progression of the disease or disorder.

As used herein, management with regard to CaHD encompasses a reduction in one or more signs and symptoms of CaHD (symptoms include dyspnea and fatigue, signs include edema and ascites), a reduction in the level of a CaHD biomarker such as N-terminal pro-B-type natriuretic peptide (NT-proBNP) or 5-HIAA, a reduction in progression of CaHD (based upon serial transthoracic echocardiograph review of valvular damage), an increase in time to valve replacement surgery, and the like.

A "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

As used herein, a level of 5-hydroxyindoleacetic acid (5-HIAA) can be measured in a urine sample or a blood sample such as a plasma sample. A urine sample as used herein is typically a 24-hour urine sample. The patient collects urine in a laboratory provided container for 24 hours. The patient should avoid food high in indoles: avocado, banana, tomato, plum, walnut, pineapple, and eggplant. A normal, healthy subject typically has a urine 5-HIAA level of up to 8 mg/24 hours. A blood sample is typically a plasma sample. The patient is typically fasted overnight prior to blood sample collection. A normal, healthy subject typically has a plasma 5-HIAA level of up to 22 ng/ml.

Treatment of Patients with Newly Diagnosed Neuroendocrine Tumors

A method of treating or managing a human patient with a newly diagnosed neuroendocrine tumor comprises periodically, after newly diagnosing the neuroendocrine tumor, measuring a level of 5-hydroxyindoleacetic acid (5-HIAA) in a plasma or urine sample from the patient, and administering a therapeutically effective amount of telotristat ethyl or a pharmaceutically acceptable salt thereof when an initial level of 5-HIAA is greater than or equal to the upper limit of normal (ULN), wherein the ULN is about 22 ng/ml for the plasma sample or 8 mg/24 hours for the urine sample.

As used herein, an "initial level of 5-HIAA" is a level of 5-HIAA prior to treatment with TE, as administration of TE is expected to reduce 5-HIAA levels.

The newly diagnosed neuroendocrine tumor can be diagnosed by blood/urine tests to determine hormone levels, biopsy, molecular testing of tumor tissue, endoscopy, endoscopic ultrasound, computed tomography scan, magnetic resonance imaging, nuclear medicine imaging, and combinations thereof. Gastrointestinal neuroendocrine tumors may be detected during scans such as endoscopy, computed tomography (CT), magnetic resonance imaging (MRI) scans, somatostatin receptor-based diagnostic imaging (Indium-111 pentetreotide imaging [OctreoScan™] or gallium Ga-68 DOTATATE (or gallium Ga-68 DOTATOC or copper Cu-64 DOTATATE), or integrated positron emission tomography [PET]/CT scanning) unrelated to the tumor.

As used herein, periodically measuring the 5-HIAA level comprises measuring the level of 5-hydroxyindoleacetic acid (5-HIAA) in a plasma or urine sample from the patient once per month to once per year, such as measuring once per month, once per quarter (every three months), once every 6 months, or once per year. In the early stages after a neuroendocrine tumor is newly diagnosed, the tumor may not secrete serotonin, and thus the 5-HIAA levels may be within the normal range. However, once the tumor begins to secrete serotonin, the levels of 5-HIAA will eventually increase to levels greater than the upper level of normal leading to CS and/or CaHD. It is at the time of 5-HIAA elevation above normal when the patient will be administered a therapeutically effective amount of telotristat ethyl.

In an aspect, the patient with the newly diagnosed neuroendocrine tumor is not exhibiting symptoms of carcinoid syndrome, specifically the patient is not exhibiting carcinoid syndrome diarrhea. In the absence of carcinoid syndrome diarrhea, a patient would not be treated with TE. In another aspect, the human patient with the newly diagnosed neuroendocrine tumor is exhibiting symptoms of carcinoid syndrome, or has been diagnosed with carcinoid syndrome, and is not being treated with telotristat. In yet another aspect, the human patient with the newly diagnosed neuroendocrine tumor is not exhibiting carcinoid syndrome diarrhea, or has been diagnosed with carcinoid syndrome diarrhea, and is not being treated with telotristat for carcinoid syndrome diarrhea.

Exemplary symptoms of CS include diarrhea, flushing, abdominal pain, wheezing, palpitations, or a combination thereof. Unlike the methods described previously, the inventors have determined that intervention with TE upon determination of elevated 5-HIAA levels, but prior to development of CS, and more specifically carcinoid syndrome diarrhea, can delay both the development of CS and CaHD in these patients.

Specific symptoms of CSD can be determined using the Bristol Stool Form scale from 1 to 7. A symptom of CSD can include a daily stool consistency of loose to watery stools five (5) times or more, average daily. Other symptoms include BM frequency, urgency and urgency.

In an aspect, administration of TE, e.g., daily administration, is started when the patient is determined to have a 5-HIAA level greater than or equal to two times the upper limit of normal. In exemplary embodiments, daily administration of TE is started when the patient has a 5-HIAA level that is three, four, five or even ten times or more or more times higher than the upper limit of normal, wherein the ULN is about 22 ng/ml for the plasma sample or 8 mg/24 hours for the urine sample. For example, patients with newly diagnosed neuroendocrine tumors should be administered TE when the 5-HIAA levels exceed 24 mg/24 hours in the urine or 66 ng/ml in plasma.

In an aspect, administering TE reduces the development of CS in the patient evidenced by BM frequency, urgency and stool consistency.

In a preferred aspect, administering TE delays or reduces the likelihood of the development of CaHD in the patient. In a typical patient, CaHD typically develops within 10 to 75 months of initial diagnosis of CS. Administration of TE starting from when initial 5-HIAA levels are determined to be greater than or equal to the upper limit of normal can delay the onset of CaHD by months or even years.

In an aspect, the method further comprises performing an echocardiogram on the patient. Echocardiogram findings characteristic of CaHD include thickened, retracted, fixed valve leaflets, tricuspid/pulmonary regurgitation and dilated right chambers of the heart.

Treatment of Patients with Early Signs of Carcinoid Heart Disease Who have not had a Heart Valve Replacement In another aspect, a method of treating a human patient with a neuroendocrine tumor comprises determining that the patient has early signs of carcinoid heart disease, measuring a level of 5-hydroxyindoleacetic acid (5-HIAA) in a plasma or urine sample from the patient, and administering a therapeutically effective amount of telotristat ethyl when the initial level of 5-HIAA is greater than or equal to the upper limit of normal (ULN), wherein the ULN is about 22 ng/ml for the plasma sample or 8 mg/24 hours for the urine sample, wherein the patient has not had a heart valve replacement, and wherein the patient is not currently receiving telotristat ethyl for the treatment of carcinoid syndrome diarrhea.

As used herein, an "initial level of 5-HIAA" is a level of 5-HIAA prior to treatment with TE, as administration of TE is expected to reduce 5-HIAA levels.

In an aspect, a patient not currently receiving TE for the treatment of carcinoid syndrome diarrhea means that the patient is not receiving TE at the time of administering a therapeutically effective amount of telotristat ethyl when the initial level of 5-HIAA is greater than or equal to twice the upper limit of normal (ULN). For example, the patient may have never received TE, or the patient may have received TE in the past, however, treatment lapsed at some time prior to elevated levels of 5-HIAA being determined.

In an aspect, the patient's CS symptoms are well-controlled. For example, the patient's carcinoid syndrome diarrhea and flushing may be reduced, or a reduced level of serum serotonin may be determined.

In an aspect, determining the patient has early signs of CaHD comprises performing an echocardiogram on the subject, and the echocardiogram shows signs of fibrosis. Echocardiogram findings characteristic of CaHD include thickened, retracted, fixed valve leaflets, tricuspid/pulmonary regurgitation and dilated right chambers of the heart. Reducing 5-HIAA levels in such patients may slow the progression of the fibrosis. In addition, cardiac magnetic resonance imaging or computerized tomography may be used to assess right heart size and function. In another aspect, the early sign of carcinoid heart disease is elevated NT-proBNP. Natriuretic peptides are substances made by the heart. Two main types of these substances are brain natriuretic peptide (BNP) and N-terminal pro b-type natriuretic peptide (NT-proBNP). Normally, only small levels of BNP and NT-proBNP are found in the bloodstream, however, high levels of NT-proBNP are associated with congestive heart failure and are an early sign of CaHD. For example, an NT-proBNP level>260 ng/mL indicate pts at high risk for developing CaHD or likely to have a diagnosis of CaHD.

In the foregoing method, the patient likely has CS, which is a precursor to developing CaHD. Further, the patient with CaHD, has not yet had a valve replacement, which is indicative of early-stage heart disease. Still further, the patient has not been receiving TE for the treatment of carcinoid syndrome diarrhea. Currently, TE is only administered to patients with carcinoid syndrome diarrhea. Advantageously, treatment of this patient population with TE is expected to manage 5-HIAA levels and prevent or delay heart valve replacement in the subject.

Treatment of Patients Who have had a Heart Valve Replacement

A method of treating a human patient with a neuroendocrine tumor comprises identifying the patient with the neuroendocrine tumor who has had a recent heart valve replacement and administering to the patient a therapeutically effective amount of telotristat ethyl. As used herein, the patient who has had a recent heart valve replacement has had the heart valve replacement within 1 month of being administered TE. That is, TE administration is started as soon as possible after heart valve replacement, and within 30 days to optimize surgical benefit. Without being held to theory, it is believed that TE takes approximately 60 days for clinical benefit, thus the sooner 5-HIAA can be suppressed by administering TE, then less damage to the new heart valve.

In an aspect, the method further comprises measuring a level of 5-hydroxyindoleacetic acid (5-HIAA) in a plasma or urine sample from the patient and increasing the therapeutically effective amount of telotristat ethyl when the level of 5-HIAA is greater than or equal to the upper limit of normal (ULN), wherein the ULN is about 22 ng/ml for the plasma sample or 8 mg/24 hours for the urine sample.

Patients with neuroendocrine tumors who have had a valve replacement live longer than patients who have severe CaHD and do not have a valve replacement. Valve replacement patients live on average for about 58 months following surgery versus non-valve replacements who may not live half as long. However, the largest morbidity/mortality risk to valve replacement patients is the risk of their new valve developing fibrosis from continued elevated levels of 5-HIAA/serotonin which leads to poor overall survival compared to patients who newly replaced valve does not develop fibrosis. The administration of telotristat is used to keep 5-HIAA levels down and reduce the risk of fibrosis to the new valve.

Dosing and Pharmaceutical Formulations

Exemplary therapeutically effective doses of TE or a pharmaceutically acceptable salt thereof in the treatment of patients with neuroendocrine tumors are at 250 to 1500 mg per day, specifically 250 or 500 or 100 or 1500 mg tid, based on TE free base. Exemplary doses include about 100, 110, 120, 125, 130, 140, 150, 160, 170, 175, 180, 190, 200, 210, 220, 225, 230, 240, 250, 260, 270, 275, 280, 290, 300, 310, 320, 325, 330, 340, 350, 360, 370, 375, 380, 390, 400, 410, 420, 425, 430, 440, 450, 460, 470, 475, 480, 490, 500, 550, 600, 650, 700, 750, 800, 850, 900, 950, 1000, 1050, 1100, 1150, 1200, 1250, 1300, 1350, 1400, 1450, or 1500 mg. In certain aspects, the TE dose is administered from one to five times per day (e.g., 1, 2, 3, 4, or 5). In certain embodiments, the TE dose is administered three times per day.

TE is administered in the form of a pharmaceutical composition, such as single unit dosage forms suitable for oral, topical, mucosal (e.g., nasal, pulmonary, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. An exemplary oral dosage form is XERMELO®.

In an aspect, the method further comprises concurrently treating the patient with a somatostatin analog (SSA). In certain aspects, the somatostatin analog is lanreotide, octreotide, pasireotide, or a combination thereof. Therapeutic dosages of the SSAs are identifiable from their label information or are otherwise determinable by the skilled artisan by known methods. While TE is typically adjunctive therapy to SSAs, in cases when SSAs are ineffective or refractory to SSAs, TE could be used as first-line therapy or as a single agent therapy.

The use of the terms “a” and “an” and “the” and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms “comprising”, “having”, “including”, and “containing” are to be construed as open-ended terms (i.e., meaning “including, but not limited to”) unless otherwise noted. “About” or “approximately” as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, “about” can mean within one or more standard deviations, or within ±10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of treating or managing a human patient with a newly diagnosed neuroendocrine tumor, wherein the human patient with the newly diagnosed neuroendocrine tumor has not been diagnosed with carcinoid syndrome or carcinoid heart disease, comprising at least quarterly, after newly diagnosing the neuroendocrine tumor, measuring a level of 5-hydroxyindoleacetic acid (5-HIAA) in a plasma or urine sample from the patient, and daily administering a therapeutically effective amount of telotristat ethyl or a pharmaceutically acceptable salt thereof to a patient having an initial level of 5-HIAA at least two times greater than the upper limit of normal (ULN), wherein the initial level of 5-HIAA is a level prior to administration of telotristat ethyl, wherein the ULN is about 22 ng/ml for the plasma sample or 8 mg/24 hours for the urine sample, and wherein administering telotristat ethyl or the pharmaceutically acceptable salt thereof to the patient delays or reduces the likelihood of the development of carcinoid heart disease in the patient.

2. The method of claim 1, wherein at least quarterly measuring the level of 5-hydroxyindoleacetic acid (5-HIAA) in a plasma or urine sample from the patient comprises measuring once per month.

3. The method of claim 1, wherein the human patient with the newly diagnosed neuroendocrine tumor is not exhibiting symptoms of carcinoid syndrome.

4. The method of claim 1, further comprising administering a somatostatin analog to the human patient.

5. The method of claim 1, wherein the neuroendocrine tumor is a tumor of the lung, liver, pancreas, small bowel, a respiratory organ, stomach, jejunum, duodenum, ileum, appendix, colon, small bowel mesentery, cecum, rectum, or a combination thereof.

6. The method of claim 1, further comprising performing an echocardiogram on the patient.

7. The method of claim 1, wherein the telotristat ethyl or the pharmaceutically acceptable salt thereof is administered at 250 to 1500 mg per day as telotristat ethyl free base.

8. The method of claim 1, wherein the telotristat ethyl or the pharmaceutically acceptable salt thereof is administered at 250 or 500 mg three times a day, as telotristat ethyl free base.

* * * * *